United States Patent [19]

Scott-Pearse

[11] Patent Number: 5,043,282
[45] Date of Patent: Aug. 27, 1991

[54] METHOD OF PRODUCING PLANT CELL LINES AND PLANT HYBRIDS

[75] Inventor: Frank Scott-Pearse, Chatham, Canada

[73] Assignee: Kingroup Inc., Chatham, Canada

[21] Appl. No.: 320,429

[22] Filed: Mar. 8, 1989

[30] Foreign Application Priority Data

Mar. 8, 1988 [CA] Canada ................................. 560827

[51] Int. Cl.⁵ .......................... C12N 5/04; A10H 4/00; A10H 1/00
[52] U.S. Cl. ........................... 435/240.49; 435/240.4; 435/240.45; 800/200; 800/205; 47/58
[58] Field of Search ................................ 47/58; 800/1; 435/240.4, 240.45, 240.49

[56] References Cited

PUBLICATIONS

Ziemborska et al. (1986). U. of Guelph–Crucifer Genetics Coop. 1986 (70) (Abstract relied on).
Hoffman et al. (1982). Theor. Appl. Genet. 61:225–232.
Downey et al. (1987). My Principles of Cultivation Development, vol. 2. Ed. Walter R. Feler. MacMillan Pub. Co. N.Y. p. 473.
Gowers, "Eucarpia Cruciferae Newsletter" vol. 5; p. 15 (1980).
Ziemborska, "Anther Culture of Rutabaga–Rape Hybrids (*Brassica Napus* SSP. Rapifera . . . "(1986) pp. 1–3 and 105–180.
Thompson, "Breeding Winter Oilseed Rape, *Brassica Napus*" In Advances in Applied Biology; vol. 7, pp. 31–35 (1983).
Gowers, "Self-Incompatibility in *Brassica Napus*" in Proceedings–Eucarpia Cruciferae 1979 Conference.
Euphytica 24 (1975) pp. 537–541 "Methods of Producing $F_1$ Hybrid Swedes"; S. Gowers.

*Primary Examiner*—Elizabeth C. Weimar
*Assistant Examiner*—Gary Benzion
*Attorney, Agent, or Firm*—Foley & Lardner

[57] ABSTRACT

A method is disclosed for producing, in a single culture, plant cells that contain a self incompatibility (SI) determinant and plant cells that do not. A selected line is crossed with a line that is homozygous for an SI determinant, and pollen or microspores from the resulting progeny are cultured to obtain haploid cells lacking that determinant. These cells can be used, respectively, to produce sister lines that, when crossed, yield SI-heterozygous foundation seed for producing a hybrid.

3 Claims, No Drawings

METHOD OF PRODUCING PLANT CELL LINES AND PLANT HYBRIDS

BACKGROUND OF THE INVENTION

The present invention relates to the production of plant cell lines by microspore or anther culture, and to a hybridization method that entails the use of plants regenerated from such cell lines ("regenerants"), thereby to exploit sporophytically controlled self-incompatibility.

Three biological methods have been employed for the production of various hybrids: cytoplasmic male sterility, genetic male sterility, and self-incompatability. Other chemical and mechanical methods have also been used. Cytoplasmic male sterility has been used to produce hybrids of oilseed rape (*Brassica napus*), while self-incompatibility is the method commonly used to produce hybrids of the vegetable Brassica crops like Brussel sprouts, cauliflower, broccoli and cabbage.

There are two types of self-incompatibility in plants, namely, sporophytic and gametophytic. The present invention relates to sporophytically-determined self-incompatibility, a condition under which pollen does not readily germinate and fertilize if it lands on the stigma of its own flowers or of the flowers of other plants carrying the same allele. The stigma of a self-incompatible plant is receptive, however, to pollen from a plant that does not contain the same self-incompatibility (SI) determinant, even though the pollen-donor plant may contain another SI determinant.

The prevention of fertilization in an incompatible pollination is due to the action of two mechanisms at the stigmatic surface. There is poor adhesion of the pollen grains to the surface and pollen tube growth is inhibited or reduced so that fertilization fails to take place. S. Gowers in PROC. EUCARPIA "CRUCIFERAE 1979" CONF. (Wageninger) 80–84 (hereafter "*Proceedings*").

In this description, the term "determinant" denotes a unit character of Mendelian heredity. Although some characters, particularly of a quantitative nature, are due to a number of genes, self-incompatibility is generally controlled by a single gene which may be dominant or recessive. In *Brassica*, for example, self-incompatibility is controlled by two genes, each represented by two alleles, at two different loci.

More specifically, self-incompatibility has been recognized in *B. napus*, see Olsson (1953) *K. Landtbr. Akad. Tidskr.* 92: 394–402, as well as in *B. campestris*, see Bateman (1955) *Heredity* (London) 9: 53–68, and in *B. cleracea*, see Thompson (1957) *J. Genet.* 55: 45–60. The use of self-incompatibility to produce a double-cross hybrid of marrow stem kale has been suggested by Thompson (1959) *Agriculture* 65: 487–91. The use of self-incompatibility as a means of producing oilseed rape was also proposed by Gowers, (1975), *Euphytica* 24: 537–41, *Proceedings* 80–84, (1980) *Eucarpia cruciferae Newslet.* 5: 15–16, who outlined a system for producing modified, double-cross F1 hybrid seed using normal and self-incompatible isogenic lines.

The maintenance of SI lines has been a major problem. There are at least three methods which can be used to overcome the self-incompatibility and, thus, to reproduce such lines: micropropagation, variation of the levels of carbon dioxide and other chemical treatments, and bud pollination. Micropropagation is a new procedure, presently being explored, that involves the reproduction of a plant from single cells or clumps of cells derived from suitable tissue. The use of carbon dioxide is one of the preferred methods. It involves the raising of carbon dioxide levels around the plant within a few hours after the pollen has landed on the stigma. While this method can be used in a greenhouse, it cannot be used on a field scale. In bud pollination, each individual flower must be dissected before it has fully developed and opened, and pollen then deposited on the immature stigma, which is receptive at this stage.

The disadvantage of each of these procedures is that the SI line, as a result of the high costs involved, can only be maintained on a small scale. Extensive field production of the hybrids using the SI line as female is impractical due to cost factors.

SUMMARY OF THE INVENTION

It is therefore an object of the present invention to provide a method for producing both normal and self-incompatible homozygous sister lines in a single procedure.

It is a further object of the present invention to provide a method of producing hybrids which is cost effective and which can be used on a commercial scale.

In accomplishing these objects, there has been provided, in accordance with one aspect of the present invention, a method for producing plant cells that contain a determinant for self-incompatibility, comprising the steps of:

a) crossing a first line with a second line that is homozygous for a determinant for self-incompatibility;

b) isolating microspore- or pollen- containing anthers from the buds of the resulting plants;

c) extracting microspores or pollen from the anthers; and d) culturing the microspores or pollen in a growth medium to obtain a single culture comprised of haploid cells that contain the self-incompatibility determinant and haploid plant cells that do not contain the self-incompatibility determinant.

In one preferred embodiment, the first line of this method is a self-compatible line, while in another preferred embodiment the first line is an inbred line.

In accordance with another aspect of the present invention, there has been provided a culture comprised of plant cells produced by the above-described method.

In accordance with yet another aspect of the present invention, a method has been provided for producing, from a single plant-cell culture, a plant line that is homozygous for a self-incompatibility determinant and a plant line that is not homozygous for the determinant, which method comprises steps (a) through (d) set out above and, additionally, the steps of (e) producing both self-compatible and self-incompatible plantlets from the aforementioned culture; and (f) using the plantlets to produce a first sister line that is self-compatible and a second sister line that is homozygous for the determinant. Also provided, in accordance with another aspect of the present invention, is a plant line produced by this method.

In accordance with another aspect of the present invention, a method has been provided for producing hybrid seed comprising the steps of:

a) crossing first and second sister, produced as described above, in order to obtain a third line that is heterozygous for a self-incompatibilty determinant, and b) crossing the third line with a line selected from the group consisting of self-compatible line and a line carrying a determinant for self-incompatibility that is different from the self-incompatibility determinant. Also provided is hybrid seed produced by this method.

DETAILED DESCRIPTION OF THE PREFERRED EMBODIMENTS

Pursuant to the present invention, both normal and self-incompatible haploid plant cells, particularly rapeseed cells are produced through the use of androgenesis, which entails anther or microspore culture. The haploid cells thus obtained are then used to produce into diploid regenerant plants, as described in greater detail below.

According to a preferred embodiment of the present invention, a chosen oilseed rape line is crossed with an oilseed rape line that is homozygous for an SI determinant. (In this context, a "line" is a group of plants with characteristics that are distinct, uniform and stable. See W. R. FEHR, 1 PRINCIPLES OF CULTIVAR DEVELOPMENT (Macmillan Publishing Co. 1987).) The chosen line is preferably an inbred line which exhibits desirable characteristics such as yield, maturity, disease resistance and other agronomic or quality characteristics. It can be a self-compatible line or one that is self-incompatible by virtue of its carrying a different SI determinant than the one carried by the self-incompatible line with which it is crossed. In any event, the lines which are crossed are preferably from generally the same genetic background, so that there can be heterosis when the progeny of the cross are themselves crossed with a line from another background.

An SI determinant used in the method of the present invention should be dominant. Moreover, it is preferred that the SI determinant corresponds to a single, dominant allele. A number of dominant SI determinants suitable for use according to the present invention have been identified in *B. napus*, as well as in progenitor species *B. campestris*, and *B. oleracea*, and have been introduced, via known procedures, into elite oilseed rape lines. A suitable SI determinant is accessible to conventional breeding techniques through plant material that is available to the public from the Scottish Plant Breeding Station, Pentlandfield (Roslin, Midlothian, U.K.), as well as from the Gene Bank Facility, Wellesbourne (Warwick, U.K.).

Seed from the aforementioned cross is grown, pursuant to the present invention, until either microspores or pollen can be extracted from the flower buds and cultured. (This procedure is known as "anther culture" when pollen is used, whereas it is known as "microspore culture" when microspores are used). The resulting cell culture is comprised of haploid cells containing the SI determinant contributed by the SI-homozygous parent of the cross, and haploid cells lacking that SI determinant. Cells containing and not containing the determinant can be distinguished, one from the other, via an electrophoretic determination of self-incompatibility proteins, for example, according to Nasrallah et al. (1970) *Genetics* 76: 45–50, or Nishio & Hinata (1977) *Heredity* 38: 391–96, the respective contents of which are hereby incorporated by reference.

Embryos produced, in a conventional manner, from cultured microspores or pollen are grown into plantlets, as described in greater detail hereinafter. The plantlets, which are haploid, may double spontaneously or can be caused to double, in accordance with conventional methodology, by treatment with a polyploidization agent.

Thus obtained are normal diploid plants and, in addition, SI-homozygous diploid plants that carry the SI determinant contributed by one of the parent lines; that is, both sister lines (lines derived from the same cross) that are required to produce hybrid parental stock are produced in one step. An SI-homozygous plant produced in this manner can be distinguished from the normal (self-compatible) plants by known techniques, e.g., by microscopic examination of the stigma after pollen shed, in order to confirm the absence of pollen tubes. See, e.g., D. De Nettancourt in MONOGRAPHS ON THEORETICAL AND APPLIED GENETICS: INCOMPATIBILITY IN ANGIOSPERMS, Vol. 3 (Springer-Verlag) and Stead et al. (1979) *Planta* 146: 211–16, the respective contents of which are hereby incorporated by reference.

Both the SI and the normal sister lines are then multiplied, as a step toward production of hybrids in accordance with the present invention. For plants of the SI line, carbon dioxide gas at a concentration of 3–10% can be used to overcome self-incompatibility at flowering time, allowing the plant's own pollen to germinate and grow on the stigma.

This exposure to elevated carbon-dioxide levels is effected in an enclosed area, such as a greenhouse or a growth room. The gas is introduced and mixed by circulating fans within three to twelve hours of the pollen being released and landing on the stigma. The length of time the pollen remains viable on the stigma varies with the temperature and humidity of the air. Hot dry conditions reduce the time. Release of the pollen can be assisted by mechanically shaking the plants and by the use of bees or other insects such as blowflies. See Taylor (1977) *Rep. Pl. Bred. Inst.* 1976-77. Extremely high humidity at the time of pollen release will slow or even stop pollen from being released and will reduce seed set. Changes in environmental conditions can also affect the SI response, as discussed, for example, by Palloix et al. (1985) *Theoret. Appl. Genet.* 70: 628–33, and by O'Neill et al. (1984), *Plant Cell Environ.* 7: 285–88.

The plants of the normal sister line are multiplied in isolation and used as pollinators in the next step, which entails production of foundation seed. When an SI sister line is pollinated in the field by its normal sister line, it produces seed that is heterozygous for the SI determinant. Since an SI determinant used according to the present invention should be dominant, plants grown from such seed are also self-incompatible and can be used in the next step of the hybrid-production process.

This next step involves planting the seeds obtained from the cross of the sister lines, to obtain SI-heterozygous plants which can function as female parents for the hybrid, along with pollinator seeds not carrying the same SI allele.

The advantage of seed production in accordance with the present invention is that only a very small amount of seed from the homozygous SI line is required to produce large quantities of commercial hybrid seeds. Three hundred to five hundred seeds planted in a greenhouse or a growth room equipped to accommodate a treatment with $CO_2$ at pollination, as described above, can produce one kilogram of a homozygous SI parent seed. When properly space-planted, in strips, in a field with seed from the normal sister-line, one kilogram of such parent seed will plant up to one hectare, from which two tonnes of foundation seed can be harvested.

Production of hybrid seed can then proceed with the planting of the foundation seed, along with seed of an appropriate pollinator, on up to 1,000 hectares, from which 2,000 tonnes of commercial hybrid seed can be harvested, sufficient to plant about 500,000 hectares at typical farm-seeding rates.

MICROSPORE AND ANTHER CULTURE

Buds 4 to 5 mm in length are removed from the terminal and the upper two axillary racemes of donor plants (preferably, F1 hybrids) that have approximately five open flowers on the terminal raceme. The buds are surface-sterilized in 5.7% hypochlorite solution for ten minutes in a horizontal laminar flow bench. After sterilization, the buds are placed in three, consecutive, five-minute rinses of autoclaved, deionized-distilled water. The buds are opened under a dissecting stereoscope with the use of sterile fine tweezers. Intact anthers are removed from the buds which have a petal-to-anther ratio between 1:2 and 2:3.

Anthers for microspore culture are bulked in liquid B5 medium, see Gamborg et al. (1968) *Exp. Call Res.* 50: 151–58, with 13% sucrose in a 30 ml beaker. Microspores are released from the anthers by macerating them with a teflon plunger. The resulting suspension is filtered through 63-micron and 44-micron Nytex filters, and the filtrate is centrifuged at 1,000 rpm for three minutes to pellet the microspores. The supernatant is removed, the microspores are resuspended with B5 and centrifuged at 1,000 rpm for three minutes. This step is repeated three times.

The final microspore pellet is resuspended with a modified Nitsch and Nitsch (1967) liquid NLN medium, see Lichter (1981) *Z. Pflanzenphysiol.* 103: 229–37; (1982) *Z. Pflanzenphysiol.* 105: 427–34, to give a microspore density of approximately 204,000 microspores per ml of suspension (approximately 12 anther equivalents per ml). One ml of microspore suspension is added to 60×15 mm Falcon plates which already containing 1.5 ml of liquid NLN, thereby provided a final microspore density of 81,600 microspores per ml. Microspore culture plates are wrapped with parafilm, placed in foil-wrapped plastic boxes and incubated at 32° C. for three days, followed by approximately 22 days at 25° C.

Anthers for anther culture are floated on 2.5 ml of M41 liquid medium, described by Keller et al. (1975) *Can. J. Genet. Cytol.* 17: 655–66, with 10% sucrose and 0.1 mg/l of 2-4D and 0.1 mg/l naphthalene acetic acid in 60×15 mm Falcon plates. Plates containing twelve intact anthers are wrapped with quadruple-thickness strips of parafilm, to prevent desiccation and contamination, and these are placed in plastic boxes. The plastic boxes are wrapped with foil to exclude light and then are incubated at 35° C. for two days, and thereafter for about 28 days at 25° C., to induce embryogenesis.

The cotyledonary embryos, see Chuong & Beversdorf (1985) *Plant Sci.* 39: 219–26, produced by microspore or anther culture are counted and transferred to solid B5 medium (2% sucrose, 0.8% agar) without hormones (B5-H), pursuant to Gamborg et al. (1968) *Exp. Cell. Res.* 50: 151–58, on 60×100 ml petri plates, at a density of ten embryos per plate.

After four weeks, the number of plantlets which develop normal shoots and roots are counted, individually labelled and transferred to sectional flats containing a suitable greenhouse potting medium. The flats are maintained in an environmentally-controlled growth room set at 23° C. day/18° C. night. Abnormal regenerants, lacking either a well developed shoot, apical meristem or root system, are explanted onto solid B5 G with 2% sucrose, 0.8% agar and 1 ml of L-1 gibberellic acid (GA), to induce normal plantlet development. After six weeks, the normal regenerants which develop are transferred to MetroMix in the growth room, and a second explant onto fresh B5 H is performed with recalcitrant material. After four weeks, the normal regenerants which develop are transferred to the growth room, while the remainder of the material is discarded.

SELECTION OF SPONTANEOUS DIPLOIDS

There are a number of cytological methods to determine the ploidy of regenerated plants. Floral morphology is one of the easiest markers to use in this regard. Regenerated plants are grown in small-sectional flats to speed their development to flowering. The spontaneous diploid plants have flowers with large petals and dehiscent anthers, whereas the haploid plants have reduced petal size and indehiscent anthers. Keller & Armstrong (1978) *Z. Pflanzenzuchtg.* 80: 100–08.

TREATMENT OF HAPLOID PLANTS WITH COLCHICINE

To induce ploidization, the roots of haploid plants produced as described above are thoroughly washed, and the lower part of the plant, including the roots, is immersed for five hours in a colchicine solution comprising 0.1% colchicine and 2–3 drops of Tween 20 per liter. The plannts are placed under fluorescent light to ensure good colchicine uptake by the roots. The plants are then removed from the colchicine solution and placed under running water for one hour or more.

While the present invention has been described in connection with a specific embodiment thereof and in a specific use, various modifications will occur to those skilled in the art. For instance, the foregoing description refers to oilseed rape, but the present invention can be used with other crops, as well such as with those of the genus *Brassica*, that display sporophytically determined self-incompatibility. I therefore wish to embody within the scope of the patent which may be granted hereon all such embodiments as reasonably and properly fall within the scope of my contribution to the art.

What is claimed is:

1. A method for producing hybrid seed comprising the steps of
   (A) providing first and second sister lines by
      (i) crossing a first line with a second line that contains a dominant determinant for sporophytically determined self-incompatibility,
      (ii) isolating microspore- or pollen-containing anthers from the buds of the resulting plants,
      (iii) extracting microspores or pollen from said anthers,
      (iv) culturing said microspores or pollen in a growth medium to obtain, in a single culture, haploid cells that contain said self-incompatibility determinant and haploid plant cells that do not,
      (v) producing both self-compatible and self-incompatible plantlets from said culture, and
      (vi) using said plantlets to produce a first sister line that is self-compatible and a second sister line that is homozygous for said determinant;
   (B) crossing said first and second sister lines to obtain a third line that is heterozygous for a self-incompatibility determinant; and (C) crossing said third line with a line selected from the group consisting of a self-compatible line and a line carrying a determinant for self-incompatibility that is different from said self-incompatibility determinant.

2. A hybrid seed that is the product of a method of claim 1.

3. An assemblage of hybrid seeds that is the product of a method of claim 1.

* * * * *